United States Patent [19]
Madni et al.

[11] Patent Number: 5,956,464
[45] Date of Patent: Sep. 21, 1999

[54] FUZZY LOGIC CONTROLLED ENDOMETRIUM ABLATOR

[75] Inventors: Asad M. Madni, Los Angeles; Lawrence A. Wan, Malibu; Jim Bi Vuong, Northridge, all of Calif.

[73] Assignee: BEI Sensors & Systems Company, Inc., Sylmar, Calif.

[21] Appl. No.: 08/634,691

[22] Filed: Apr. 18, 1996

[51] Int. Cl.$^6$ .............. G06F 9/44; A61M 31/00; A61F 7/00
[52] U.S. Cl. .............. 395/61; 395/900; 604/54; 604/55
[58] Field of Search .............. 604/65, 67, 54, 604/55, 48; 395/61, 900, 3; 364/148

[56] References Cited

U.S. PATENT DOCUMENTS

| | | | |
|---|---|---|---|
| 4,867,375 | 9/1989 | Ueki et al. | 236/12.12 |
| 4,949,718 | 8/1990 | Neuwirth | 128/401 |
| 5,149,472 | 9/1992 | Suganuma | 264/40.6 |
| 5,179,625 | 1/1993 | Hisano | 395/61 |
| 5,184,292 | 2/1993 | Schneider | 364/162 |
| 5,242,390 | 9/1993 | Goldrath | 604/55 |
| 5,277,201 | 1/1994 | Stern | 607/98 |
| 5,345,776 | 9/1994 | Komazaki et al. | 62/176.3 |
| 5,437,629 | 8/1995 | Goldrath | 604/21 |
| 5,451,208 | 9/1995 | Goldrath | 604/55 |
| 5,600,553 | 2/1997 | Kawasaki et al. | 395/61 |

OTHER PUBLICATIONS

J. Tombs, et al., "Design of a Fuzzy Controller Mixing Analog and Digital Techniques," Proc. Third IEEE Conf. on Fuzzy Systems, vol. 3, pp. 1755–1758, Jun. 1994.

L. Fortuna, et al., "Neural Modeling and Fuzzy Control: an application to control the temperature in a thermal process," Second IEEE Int'l. Conf. on Fuzzy Systems, vol. 2, pp. 1327–1333, Mar. 1993.

R. Stobart, "Tutorial on Fuzzy Control," IEE Colloquim on 'Two Decades of Fuzzy Control—Part 1', pp. 1/1–6, May 1993.

M. Khalid, et al., "Temperature Regulation with Neural Networks and Alternative Control Schemes," 1994 IEEE Int'l. Conf. on Neural Networks, vol. 4, pp. 2599–2604, Jun. 1994.

J.G. Dawson and Z. Gao, "Fuzzy Logic Control of Variable Time Delay Systems with a Stability Safe Guard," Proc. 4th IEEE Conf. on Control Applications, pp. 347–353, Sep. 1995.

J. Wilkinson, "Additional Advances in Fuzzy Logic Temperature Control," Conf. Record of the 1995 IEEE Industry Applications Conf., vol. 3, pp. 2721–2725, Oct. 1995.

*Primary Examiner*—Robert W. Downs
*Attorney, Agent, or Firm*—Jerry G. Wright; Flehr Hohbach Test Albritton and Herbert LLP

[57] ABSTRACT

A fuzzy logic controller for a endometrium ablator heat a liquid to 85° C. which is continuously circulated into the uterus to ablate the endometrium. The fluid temperature is maintained by the fuzzy logic controller which has as its inputs the temperature of the fluid and its rate of change of temperature. Associated membership functions, cold, cool, warm, hot for temperature, and negative and zero and positive for rate are respectively provided. Appropriate rules are then provided and defuzzification with the use of a singleton output function yields an output signal which controls temperature by pulse width modulation.

6 Claims, 6 Drawing Sheets

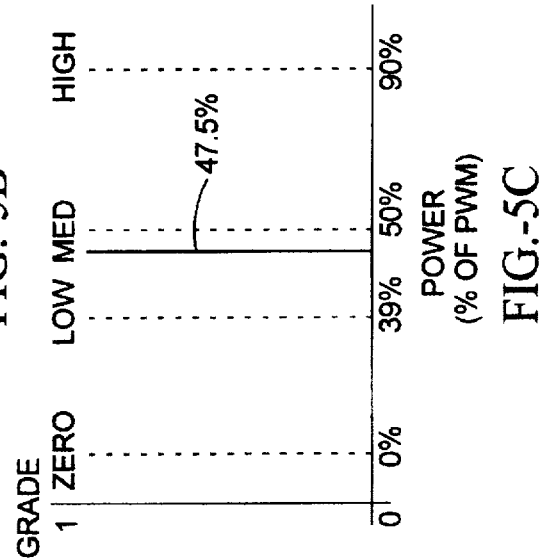
FIG.-5B
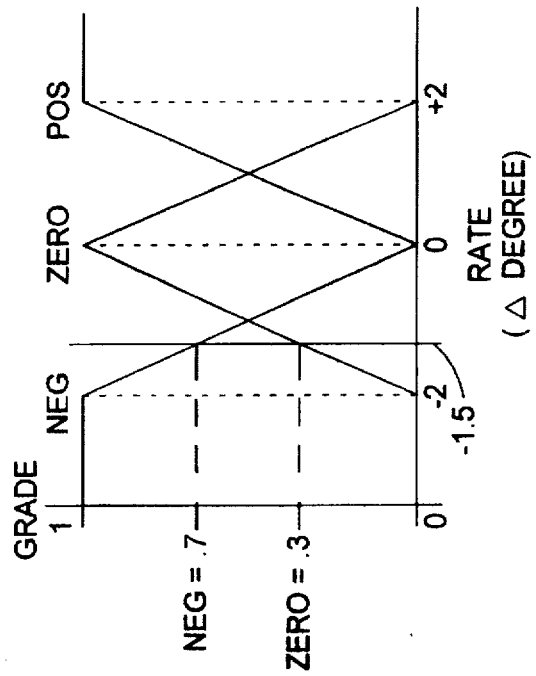
FIG.-5A
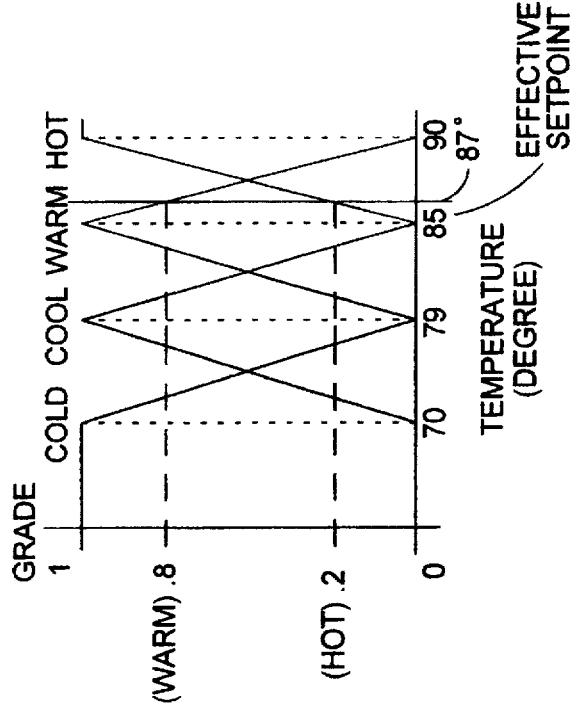
FIG.-5C
$$PWM\% = \frac{.7*.5 + .2*.39}{.7 + .2} = 47.5\%$$
FIG.-5D

1. IF TEMP IS COLD THEN POWER IS HIGH.

2. IF TEMP IS COOL AND RATE IS POSITIVE THEN POWER IS LOW.

3. IF TEMP IS COOL AND RATE IS NEGATIVE THEN POWER IS HIGH.

4. IF TEMP IS COOL AND RATE IS ZERO THEN POWER IS MEDIUM.

5. IF TEMP IS WARM AND RATE IS POSITIVE THEN POWER IS LOW.

6. IF TEMP IS WARM AND RATE IS NEGATIVE THEN POWER IS MEDIUM.

7. IF TEMP IS WARM AND RATE IS ZERO THEN POWER IS LOW.

8. IF TEMP IS HOT AND RATE IS POSITIVE THEN POWER IS ZERO.

9. IF TEMP IS HOT AND RATE IS NEGATIVE THEN POWER IS LOW.

10. IF TEMP IS HOT AND RATE IS ZERO THEN POWER IS ZERO.

FUZZY LOGIC CONTROLLED ENDOMETRIUM ABLATOR

The present invention is directed to a fuzzy logic controlled endometrium ablator and more particularly where a hot circulating fluid has its temperature controlled or maintained by fuzzy inference logic.

BACKGROUND OF THE INVENTION

U.S. Pat. Nos. 5,242,390, 5,451,208 and 5,437,629 all disclose a technique of endometrial ablation where a hot circulating fluid which continuously circulates into and out of the uterine cavity ablates the endometrium. The temperature of the fluid is 85° C. and is maintained at that temperature by a cartridge heater.

As discussed in the above '208 patent the control means for regulating the liquid temperature can be that of a conventional thermostat controlled heater. A more automated system using conventional computer control is disclosed in Pat. No. 4,949,718 which is directed to a different type of apparatus where fluid does not directly contact the endometrium.

OBJECT AND SUMMARY OF THE INVENTION

It is an object of the present invention to provide a fuzzy logic controlled endometrium ablator.

In accordance with the above object there is provided fluid delivery apparatus for use in performing hysteroscopic endometrial ablation where fluid heated to a predetermined temperature to produce ablation is continuously circulated into and out of the uterine cavity. The apparatus comprises a fluid source with pumping means for circulating the fluid. Heater means maintain the circulating fluid at the predetermined temperature. The temperature of the circulating fluid and rate of change of the temperature is sensed. Controller means are provided responsive to inputs of the temperature of the circulating fluid and the rate of change for providing an output control signal to the heater means to substantially maintain the predetermined temperature including digital logic means for providing first and second input membership functions respectively related to the inputs and which are formed by mathematically fuzzy sets and for determining the degree of membership of the inputs to the input membership functions. The digital logic means also stores a set of rules which take into account the heat transfer characteristic of the ablation process. The digital logic means also provides an output membership function from which may be selected the output control signal, the controller means selecting only the rules relevant to the inputs having a degree of membership with the input membership functions and also using the output membership function for finding a weighted average which is the output control signal.

BRIEF DESCRIPTION OF THE DRAWINGS

FIG. 5A is an input membership function diagram illustrating a step of FIG. 4.

2

Figure 4:
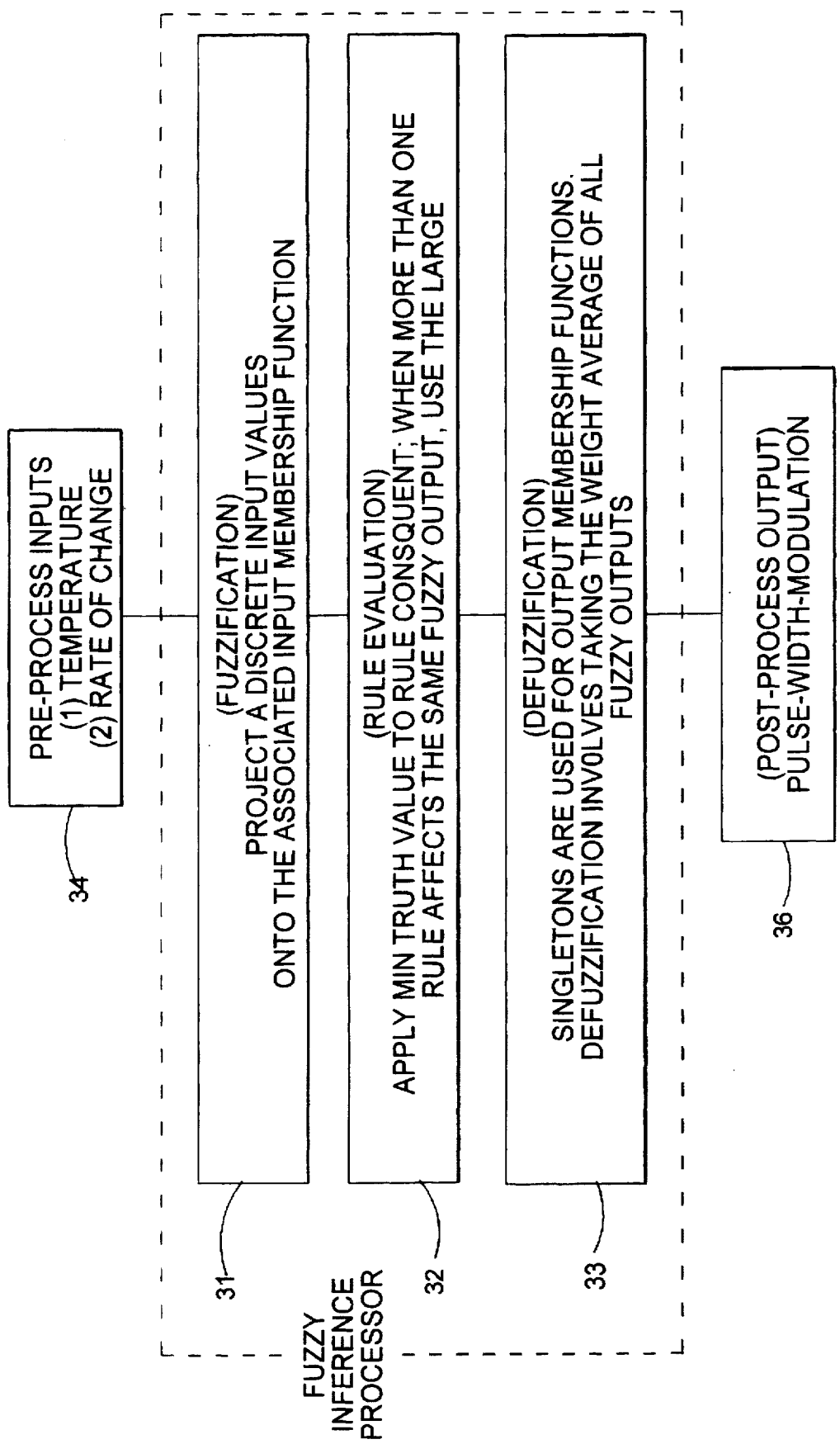
FIG. 4 is a flow chart illustrating in broad terms the operation of the present invention.

FIG. 5B is another input membership function diagram illustrating a step of FIG. 4.

FIG. 5C is an output membership function diagram illustrating a step of FIG. 4.

FIG. 5D is an equation illustrating another step of FIG. 4.

FIG. 6 is a set of rules for a step of FIG. 4.

Figure 7:
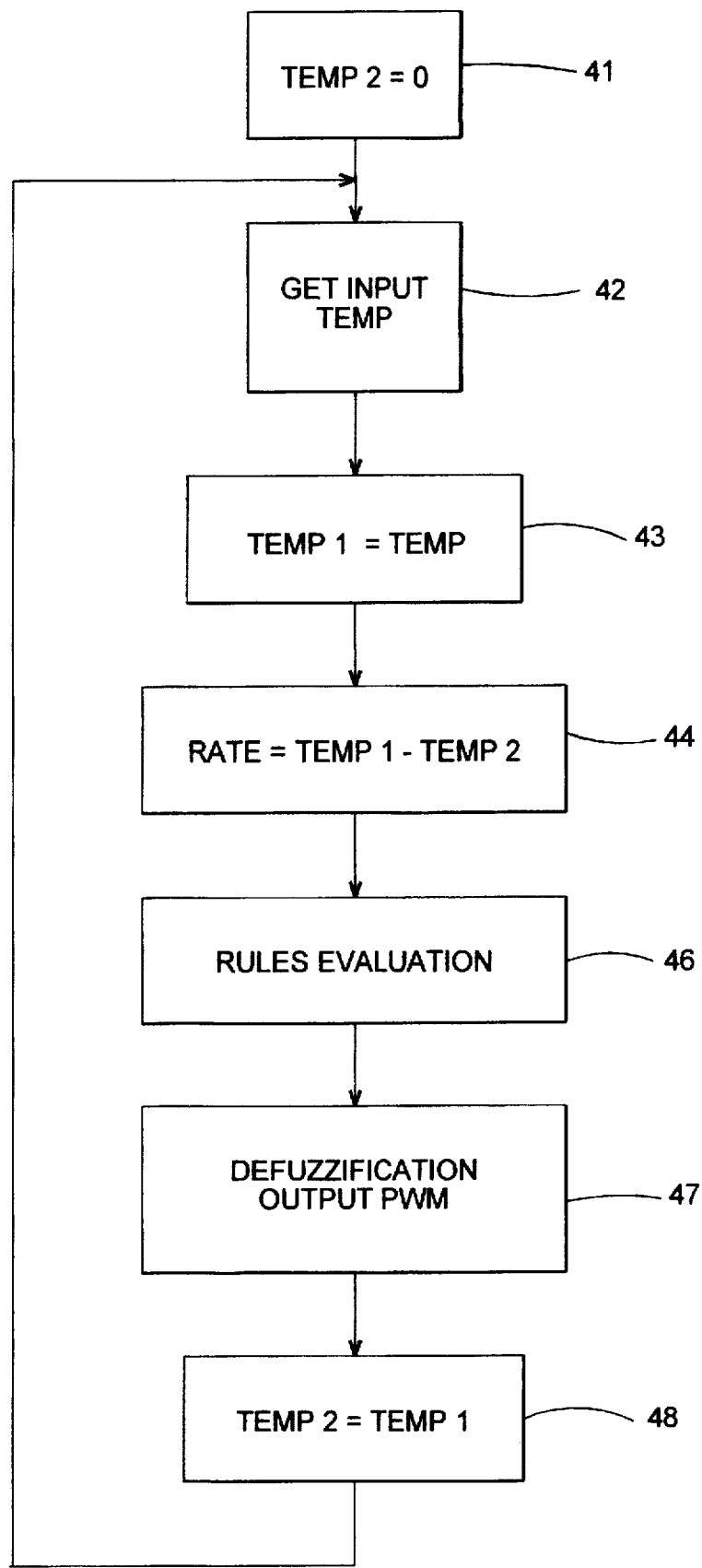

FIG. 7 is a flow chart illustrating in more detail the operation of FIG. 4.

Figure 1:
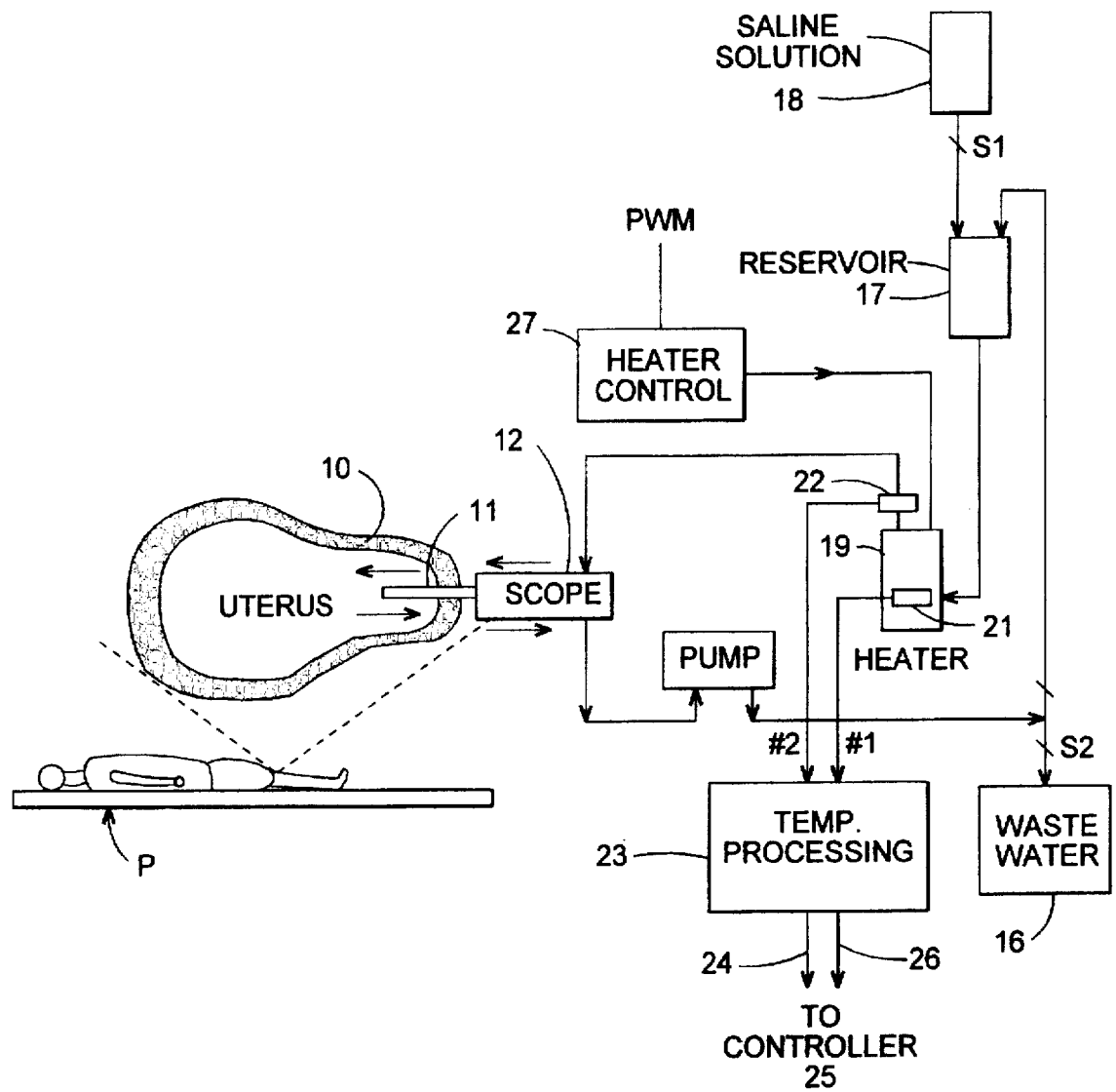
FIG. 1 is a schematic diagram of a closed loop embodiment of the apparatus of the present invention.

FIG. 1 illustrates the apparatus for practicing the technique of the present invention on a patient, P, on whom thermal ablation of the endometrium of the uterus 10 is being conducted in accordance with the patents discussed above. A hysteroscopic sheath 11, as discussed in the above patents, provides a heated fluid flow which continuously circulates as shown by the direction of arrows into and out of uterus 10. (The fluid flow channels are not shown).

A visual scope 12 connected to sheath 11 provides a medical doctor a visual view of the process. Fluid flows through the scope on line 14 and then through a pump 13 to a heater 19. The fluid is typically water. Reservoir 16 for waste water is provided with a valve S2 which continues to a second reservoir 17 which receives a saline solution from a container 18. The fluid proceeds through a heater 19 of the cartridge type which has in the heater a pair of temperature sensing probes 21 and 22. The probes may be thermistors of the Balco type. The output of each probe is connected via lines #1 and #2 to a temperature processing unit 23 which then provides on line 24 a combined fluid temperature, T, and on line 26 a rate of change of temperature measured as will be discussed below as a positive, negative or zero rate per unit time. In normal operation the temperature of the two probes should be almost identical; if not, a system malfunction is flagged.

Finally the output of heater 19 is connected to scope 12 on line 14 to complete the circulating system. To control the temperature of heater 19 there is a heater control unit 25 which is driven on its input line by a PWM (pulse width modulated) signal to determine the final predetermined temperature of the circulating liquid. In the past, hardware techniques using PID (proportional integral derivative) have been used to generate a PWM signal.

Figure 3B:
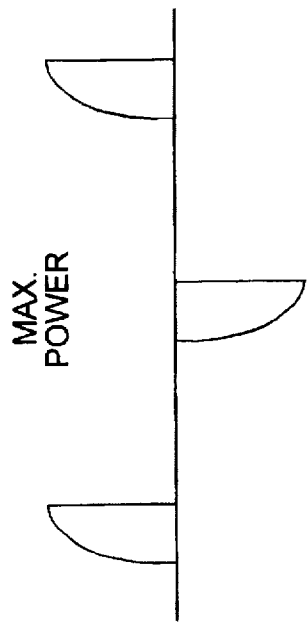
FIGS. 3A through 3D are waveforms present in the heater portion of FIG. 1.
Figure 3D:
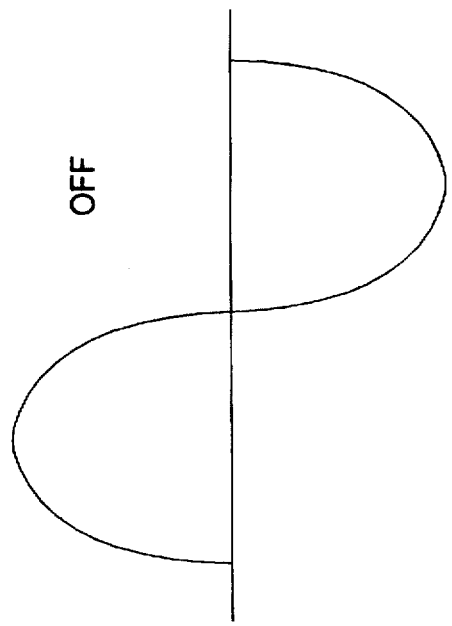
Figure 3A:
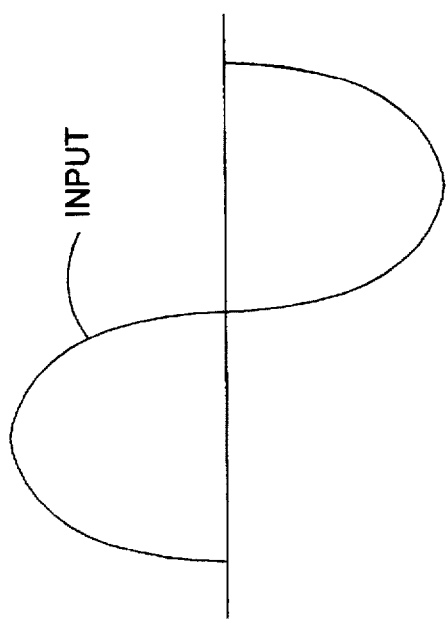
Figure 3C:
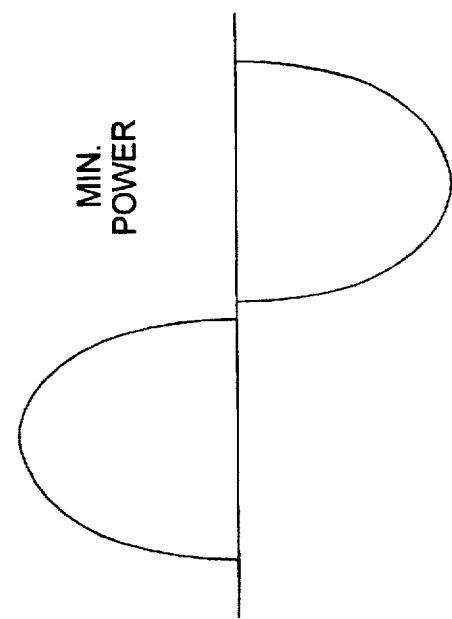

Referring briefly to FIGS. 3A through 3D, the PWM signal when off is illustrated in FIG. 3D. FIG. 3A is the voltage input to the heater coil, and FIGS. 3B and 3C illustrate maximum and minimum power applied to the heater coil as determined by the PWM input.

Figure 2:
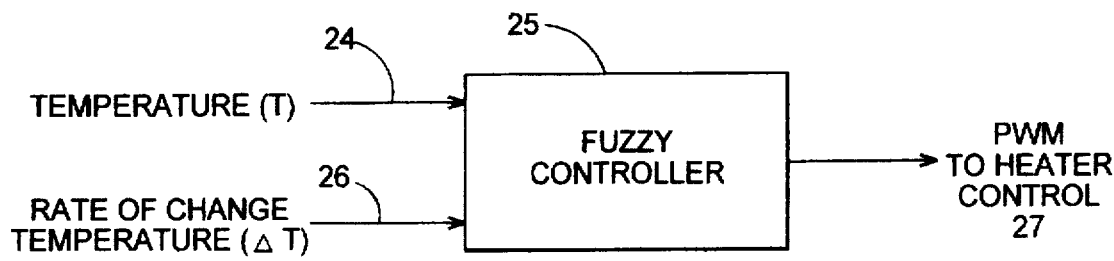
FIG. 2 is a block diagram illustrating the fuzzy controller of the present invention showing how it interfaces with FIG. 1.

As stated above such PWM signals previously had been derived by very typical PID hardware techniques. However, in accordance with the present invention, as illustrated in FIG. 2, the inputs of temperature T, 24 and delta T, 26, are now processed by a fuzzy controller unit 27 to provide a PWM signal. The fuzzy controller as will be described below provides an "intelligent" microcontroller based system which is a simple and elegant solution to maintaining a constant 85° C. temperature during the ablation process. Such fuzzy logic allows a control system which is inexpensive, simple, more reliable, and more accurate than straightforward software PID techniques where the physics of the entire system must be mathematically modeled.

Before describing the fuzzy logic technique in detail, it should be initially stated that the phrase "fuzzy logic" is actually a misnomer. There is nothing fuzzy about it and a better name would be "multi-valued logic". It is related to mathematical fuzzy set theory, developed by Lofti Zadeh at the University of California at Berkeley, Calif. Thus, terms to be used below are well known in the fuzzy logic field.

Referring now to FIG. 4, fuzzy inference is accomplished in three stages. First there is in step 31 a fuzzification, in step 32 a rule evaluation and then in step 33 a defuzzification. Step 34 illustrates this preprocessing of inputs (see unit 23 of FIG. 1) where a temperature and rate of change are derived form the process to be controlled. Then as illustrated in step 36, labeled post process output, a PWM output control signal is provided which, of course, is the input for heater control unit 27 of FIG. 1 to control the predetermined desired temperature of the circulating liquid.

Briefly in step 31, the fuzzification step, input variables, that is, temperature and rate of change, are discrete input values which are assigned degrees of membership in various membership function or classes. Thus, the temperature input is assigned membership, according to degrees of coldness, coolness, warmth or hot as shown in FIG. 5A. The horizontal axis is the temperature of the circulating fluid and the vertical axis is the degree of membership ranging from zero to one. As illustrated the member- ship functions or fuzzy sets are triangularly shaped. Other membership shapes depending on the resolution and response desired may be trapezoidal or, as illustrated in FIG. 5C, which is an output membership function of the PWM power, a mathematical singleton at 0%, 39%, 50% and 90% power.

The output membership function of FIG. 5C is described in step 33 and described as the defuzzification step where the fuzzy outputs are mathematically combined to provide a discrete value needed for a pulse width modulation waveformed to drive the heater.

The other input membership function is illustrated in FIG. 5B; again formed by triangular waveforms, which is the rate of change of temperature which has rates of negative, zero and positive.

Referring finally to rule evaluation step 32 of FIG. 4, inputs; are applied to a set of rules (see FIG. 6) and the results of the various rules generate a set of fuzzy outputs. And this is done as will be discussed below with well known steps in fuzzy logic theory. In the defuzzification step 33, this involves taking the weighted average (in this specific case) of all fuzzy outputs. In general the defuzzification step determines a crisp value for the output variable which, in this case, is power (% PWM). There are many different ways to defuzzify the outputs in addition to the use of singletons. This includes extracting the center of gravity of the output from each rule, calculating the mean of the maximum from each rule, or a winner take all approach. It is believed the approach in the present invention is optimum for this application. Thus in summary, referring to FIG. 4, the steps 31, 32, and 33 are in effect a fuzzy inference processor.

Referring to FIGS. 5A, 5B and 5C, these are graphical representations for applications of the rules of FIG. 6. The essential rules for the process, once it is started, are actually 5, 6, 7, and 8 (as will be discussed below in the examples) with rules 1 through 4 dealing with warmup, and rules 8 through 9 with a very hot temperature. Thus for a simpler type set of rules, rules 1 through 4 could be reduced to the following:

If temperature is cool then power is medium.

Similarly the over temperature rules 8, 9 and 10 would be reduced to the following single rule:

If temperature is hot then power is zero.

The purpose of more detailed rules 8, 9 and 10 is to prevent any possible oscillation in the feedback control system.

The membership functions illustrated in FIG. 5A, 5B, and 5C are illustrative of the advantages of a fuzzy logic control system in that it allows the designer to concentrate on how the process should be controlled. It is not necessary to first develop a mathematical model for how the control process operates but rather allows expert knowledge of the controller behavior to be easily integrated in the control strategy. And this has been done by use of the triangular input functions which are fuzzy sets for both temperature and rate of change of temperature.

EXAMPLE

The following example, referring to FIG. 5A assumes, that the present temperature is 87° C. as indicated by the vertical line. The effective set point or predetermined temperature is 85° C.; in the present invention this occurs with the input membership function for "warm" where the grade or percent membership function is a "one" or maximum. The rules (FIG. 6) are derived by the expert intuitively from the desire to maintain this effective set point and effectively accomplished by rules 5, 6 and 7 where for the warm fuzzy set the rate of power is low for a positive rate of change and medium for a negative rate of change. And when the rate of change is zero, the power is low. (Referring to FIG. 5C this means 39% power which barely compensates for radiation losses in the system). Thus this illustrates by intuitive knowledge of the system how appropriate rules may be derived. It also illustrates how the low power range in FIG. 5C is selected.

With an actual temperature of 87°, as indicted by the vertical line, there is a multi-valued output of 0.8 (WARM) and 0.2 (HOT). Then referring to FIG. 5B, assuming a rate of −1.5 as indicated, with the sets of negative and zero there are two outputs; the first being a 0.7 (NEG) and then a 0.3 (ZERO). Table I below illustrates the application of the relevant rules 6, 7, and 9 and 10 to produce the fuzzy outputs.

TABLE I

| RULE | TEMP. | RATE | OUTPUT |
| --- | --- | --- | --- |
| 6 | .8(WARM) | .7(NEG) | .5(MED) = .7 * .5 |
| 7 | .8(WARM) | .3(ZERO) | .39(LOW) = .3 * .39 |
| | | MAX .7 * .5 = .35 | |
| 9 | .2(HOT) | .7(NEG) | .39(LOW) |
| 10 | .2(HOT) | .3(ZERO) | 0(ZERO) = .2 * 0 |
| | | MAX .2 * .39 = .078 | |

$$\text{CRISP OUTPUT} = \frac{.7 * .5 + .2 * .39}{.7 + .2} = 47.5\%$$

For example, rule 6 states that if the temperature is WARM and rate is NEG then power is MEDIUM. (See Table I). The same is applicable to rules 7, 9 and 10. Rules 6 and 7 are grouped together since they have the same main temperature input (0.8 WARM) and rules 9 and 10 are grouped together with the same temperature input (0.2 HOT). This is standard procedure for fuzzy logic. This temperature is the variable to be controlled.

Then as stated in FIG. 4, in step 32, the minimum truth value is applied to the rule consequent, the pertinent rules 6, 7, 9 and 10. For rule 6 the minimum value as given 0.7*0.5. This is opposed to using 0.8*0.5. For rule 7 it is 0.3*0.39. Then in accordance with fuzzy logic procedure, when more than one rule affects the same fuzzy output, use the larger as stated in step 32 in FIG. 4. Thus rules 6 and 7 have been grouped together and provide a max using of 0.35. The same is true of rules 9 and 10 when the max is 0.078. Finally it is illustrated by Table I (and FIG. 5D) the crisp output is 47.5% which is a weighted average of the max fuzzy outputs. Thus referring to FIG. 5C the final weighted output is 47.5% which is the percent pulse width modulation.

This crisp output as illustrated by its equation is a weighted average which is a summary of fuzzy outputs multiplied by a singleton position on the horizontal axis of FIG. 5C and divided again by the sum of the fuzzy outputs.

The foregoing example is, of course, actually accomplished by the fuzzy controller 25 with proper software. And with such software specific lines of programming may be derived by using, for example, a tool such as fuzzy Tech from Inform Software Corporation. This allows designers to enter the membership functions (i.e., FIGS. 5A, 5B and 5C) and the rules of FIG. 6 graphically, and then to simulate the resulting controller, and the tool automatically generates code for a target microcontroller.

As discussed above, other output membership functions may be used such as center of gravity of the output from each rule or calculating the mean of maximums from each rule. But the singleton function is believed optimal for this application.

FIG. 7 is a flow chart illustrating a more detailed flow chart than FIG. 4 where in step 41 it is assumed that the preview temperature is zero. The input temperature in step 42 is gotten and named Temp 1 in step 43. Then Temp 2 is subtracted from Temp 1 to produce the Δ rate 44. The Rules evaluation is made in step 46, defuzzification in step 47 and then Temp 2 is renamed Temp 1 to start the next loop. The microcontroller software would store the membership functions of FIGS. 5A, B, and C, generally as end points and a slope.

Thus a fuzzy logic controlled endometrium ablator has been provided.

What is claimed is:

1. Fluid delivery apparatus for use in performing hysteroscopic endometrial ablation where fluid is continuously circulated into and out of the uterine cavity, said apparatus comprising:

a fluid source;

pumping means for circulating said fluid;

heater means for maintaining said circulating fluid at said predetermined temperature;

means for sensing the temperature of said circulating fluid and rate of change of said temperature;

controller means responsive to inputs of said temperature of said circulating fluid and said rate of change for providing an output control signal to said heater means to substantially maintain said predetermined temperature including digital logic means for providing first and second input membership functions respectively related to said inputs which are formed by mathematical fuzzy sets and for determining the degree of membership of said inputs to said input member ship functions, said first input membership function including a plurality of mathematical fuzzy sets related to said temperature of said fluid being cold, cool, warm and hot, said second input membership function being related to said rate of change in temperature and having fuzzy sets including negative, zero and positive;

said digital logic means also storing a set of rules which take into account the heat transfer characteristic of the ablation process, said digital logic means also providing an output membership function including the fuzzy sets of zero, low medium, and high power, such power being the heating power of said heater means, from which may be selected a said output control signal, said controller means selecting only said rules relevant to said inputs having a degrees of membership with said input membership functions and also using said output membership function for finding a weighted average which is said output control signals, said set of rules including the following:

a) if temperature is cool the power is medium b) if temperature is warm and rate is positive power is low c) if temperature is warm and rate is negative power is medium d) if temperature is warm and rate is zero then power is low, and e) if temperature is hot power is zero.

2. Apparatus as in claim 1 where said first input membership function varies in degree of membership from zero to one and provides a "one" or maximum membership for said warm fuzzy set at said predetermined temperature.

3. Apparatus as in claim 1 where said rule a) includes the following more detailed rules:

a) if temperature is cold then power is high b) if temperature is cool and rate is positive then power is low c) if temperature is cool and rate is negative then power is high d) if temperature is cool and rate is zero then power is medium.

4. Apparatus as in claim 1 where said rule e) includes the following more detailed rules:

a) if temperature is hot and rate is positive then power is zero b) if temperature is hot and rate is negative then power is low c) if temperature is hot and rate is zero then power is zero.

5. Apparatus as in claim 1 wherein said output membership function is formed of mathematical singletons.

6. Fluid delivery apparatus for use in performing hysteroscopic emdometrial ablation where fluid is continuously circulated into and out of the uterine cavity, said apparatus comprising:

a fluid source;

pumping means for circulating said fluid;

heater means responsive to a pulse width modulated (PWM) control signal, the percent of modulation being proportional to the heating power for maintaining said circulating fluid at said predetermined temperature;

means for sensing the temperature of said circulating fluid and rate of change of said temperature;

controller means responsive to inputs of said temperature of said circulating fluid and said rate of change for providing said PWM control signal to said heater means to substantially maintain said predetermined temperature including digital logic means for providing first and second input membership functions respectively related to said inputs which are formed by mathematical fuzzy sets and for determining the degree of membership of said inputs to said input member ship functions;

said digital logic means storing a set of rules which takes into account the heat transfer characteristic of the ablation process;

said digital logic means also proving an output membership function from which may be selected a said PWM control signal, said controller means selecting only said rules relevant to said inputs having a degree of membership with said input membership functions and also using said output membership function for finding a weighted average as a mathematical percent which is the actual percent of pulse width modulation whereby said PWM control signal is directly provided.

* * * * *